(12) United States Patent
Akizuki et al.

(10) Patent No.: US 7,324,137 B2
(45) Date of Patent: Jan. 29, 2008

(54) SYSTEM FOR AUTOMATICALLY GENERATING CONTINUOUS DEVELOPED STILL IMAGE FROM VIDEO IMAGE OF INNER WALL OF TUBULAR OBJECT

(76) Inventors: Naomichi Akizuki, c/o Emaki Incorporated, 5-36, Oitemachi, Aizuwakamatsu-Shi, Fukushima 965-0873 (JP); Naomi Yoshida, 1-1436-506, Kaijin-Minami, Funabashi-Shi, Chiba 273-0024 (JP); Agus Suharno, Studione Aizuwakamatsu 906, 2-6, Honmachi, Aizuwakamatsu-Shi, Fukushima 965-0862 (JP)

( * ) Notice: Subject to any disclaimer, the term of this patent is extended or adjusted under 35 U.S.C. 154(b) by 840 days.

(21) Appl. No.: 10/769,375

(22) Filed: Jan. 29, 2004

(65) Prior Publication Data

US 2005/0168593 A1 Aug. 4, 2005

(51) Int. Cl.
*G06K 9/36* (2006.01)
*H04N 5/235* (2006.01)

(52) U.S. Cl. .................... 348/221.1; 382/284
(58) Field of Classification Search ............. 348/221.1, 348/77, 85, 220.1; 382/100, 284, 268, 154; 345/629
See application file for complete search history.

(56) References Cited

U.S. PATENT DOCUMENTS 5,999,662 A * 12/1999 Burt et al. ................. 382/284

6,522,787 B1 * 2/2003 Kumar et al. ............... 382/268
6,912,293 B1 * 6/2005 Korobkin .................... 382/100
2004/0169663 A1 * 9/2004 Bernier ...................... 345/629
2005/0089213 A1 * 4/2005 Geng ......................... 382/154

FOREIGN PATENT DOCUMENTS

| JP | 06-42300 | 2/1994 |
| JP | 11-66316 | 3/1999 |
| JP | 11-81879 | 3/1999 |
| JP | 11-294065 | 10/1999 |
| JP | 2001-43353 A | 2/2001 |
| WO | 98/34195 | 8/1998 |
| WO | 2005/032355 A1 | 4/2005 |

* cited by examiner

Primary Examiner—Gims Philippe
(74) Attorney, Agent, or Firm—Ladas & Parry, LLP

(57) ABSTRACT

An image processing system automatically generates a seamless and continuous developed still image with little distortion by creating a developed diagram in the circumferential direction of a tube from one frame of a video image of an inner wall of a tubular object photographed by a video camera while moving in the axial direction of the tubular object and stitching the developed diagrams with each other in the longitudinal direction (i.e., on a central axis) of the tube by mosaic processing.

8 Claims, 8 Drawing Sheets

FRAME

DEVELOPED IMAGE

SYSTEM FOR AUTOMATICALLY GENERATING CONTINUOUS DEVELOPED STILL IMAGE FROM VIDEO IMAGE OF INNER WALL OF TUBULAR OBJECT

BACKGROUND OF THE INVENTION

1. Field of the Invention

The present invention relates to a system for automatically generating a seamless and continuous developed still image by generating a developed diagram in the circumferential direction of a tube based on one frame of a video image of an inner wall of a tubular object photographed while moving in the axial direction of the tubular object, and then, stitching the developed diagrams in the longitudinal direction (i.e., on a central axis) of the tube by mosaic processing in order to examine the inner wall of the tubular object.

2. Description of the Related Art

The inner wall of a tunnel, which is one kind of tubular objects (for example, a building structure such as a tunnel, a water supplying pipe and tubular organs of human beings or animals such as esophagus, stomach, large intestine, small intestine, rectum, blood vessel, urethra, ureter, urinary bladder and trachea are regarded as the tubular objects in wide sense) has been conventionally examined by direct observation by a person in the site and sketch accompanied therewith or the like. However, this has been a hard, dirty and dangerous work, requiring much manpower and much time, and further, it has been difficult to accurately specify an abnormal portion.

Therefore, in order to relieve a person of such work in the tunnel, there have been proposed several examining methods based on an image photographed by a camera.

For example, in a method disclosed in Japanese Patent Application Laid-open No. 6-42300, a curved mirror is used, a wall surface of a tunnel reflected on the curved mirror is photographed by a camera, obtained images in a tunnel circumferential direction are arranged according to a camera movement distance, thereby forming developed images of the tunnel. Here, it is necessary to design the shape of the curved mirror or optically design a lens in the camera according to the cross-sectional shape of the tunnel, thereby raising a problem of a complicated design work since the cross-sectional shape of the tunnel is not constant. Moreover, the tunnel in the circumferential direction at a certain position in an advancing direction is reflected on the curved mirror, and then, it is photographed by a single camera, thereby inducing a disadvantage of a low resolution of the image.

In the meantime, such a method has been proposed that the image reflected on the curved mirror is not photographed, but a line sensor camera is fixed to a rotary device installed inside of a tunnel, an image of a wall surface of the tunnel is obtained by scanning the tunnel wall surface in the circumferential direction thereof, and the images obtained by repeating the photographing in the same manner after movement by a predetermined distance in a tunnel axial direction (i.e., a movement direction) are combined with each other, to form a continuous developed image in the tunnel axial direction in order to directly photograph a cross-sectional shape. Such a method has been proposed in, for example, Japanese Patent Application Laid-open No. 11-294065 or 11-81879, which raises problems that a special and expensive camera is used, and further, that a photographing time becomes long.

Moreover, the tunnel is not photographed several times at predetermined angles by rotating the single camera in the axial direction, as described above, but there has been proposed a method for setting four line sensor cameras at substantially the center of the tunnel in different directions, so as to photograph the entire circumference of a wall surface of the tunnel at four sections, as disclosed in, for example, Japanese Patent Application Laid-open No. 2001-43353. However, this method requires the four expensive cameras having a wide angle, thereby raising a problem of marked laboriousness of adjustment of photographing conditions of the four cameras such as the position, direction and moving speed of the camera.

In order to solve the above-described problems, there has been proposed a method for creating a circumferentially developed diagram of each of frames of an image (photographed in a doughnut-like form) of the inner wall of a tunnel photographed by a video camera, which moves in the axial direction of the tunnel, and combining a plurality of the developed diagrams in an advancing direction (i.e., the axial direction), so as to obtain a continuous developed image in the axial direction of the tunnel, as disclosed in Japanese Patent Application Laid-open No. 11-66316.

However, such a method raises the following problems:

(1) Complicated procedures such as control of the attitude and capture of positional information of the camera are required.

This is because a computer regards all of video information as numerical values. It is necessary to accurately feedback the attitude or positional information of the camera causing a factor of fluctuations of the image as the numerical values in processing a continuous video image with a time change in high quality.

Therefore, data output from a sensor must be simultaneously acquired by mounting a sensor (e.g., a gravity sensor, a gyroscopic sensor or the like) capable of acquiring the attitude information on the side of the camera, thereby requiring a special camera device. Furthermore, a sensor for acquiring the positional information or traveling distance data (i.e., a cable sending quantity) is mounted, so that the information or data is superimposed on the image by a character generator. It is necessary to recognize the superimposed character in order to acquire the positional information or traveling distance data. However, character recognizing processing requires immense labor, and further, there might be a danger of a data loss caused by erroneous recognition.

(2) Since the frames are merely connected to each other, no seamless mosaic image can be obtained.

(3) Since the frames are merely connected to each other, the lateral (i.e., longitudinal) size of the image between the frames cannot become constant if a photographing movement speed is not constant, thereby causing the distortion of the image.

(4) Since a distorted portion and a non-distorted portion are superimposed on the image at the same portion if mosaic processing is performed by the use of all of the frames, it is necessary to classify images which are used or not used in the developed diagram by eyes of a person. Therefore, the mosaic processing (i.e., image stitching/image alignment) cannot be automatically performed, thereby raising a problem that it takes a long time.

Moreover, when a tubular organ as one kind of tubular objects is diagnosed by an endscope, an image of an affected part and its vicinities in an inner wall are frequently photographed by a small-sized CCD camera on a medical worksite. The photographed image is, in some cases, displayed on a display as a video image, or a part of a video frame is, in other cases, printed as a still image for use. In the former case, there are drawbacks that it is inconvenient to store the image together with a chart or the like, and further, that it is impossible to accurately grasp the positional relationship of the affected part with the inlet of an organ. In the latter case, since the sequential images are taken out as several pieces of partial photographs, it is difficult to grasp the entire image, and further, high-grade expert knowledge or experience is required to determine that the part corresponds to which part of the entire image. Moreover, since the number of photographs to be printed is limited, the photographs near the affected part are inevitably main, thereby causing a possibility of overlooking metastasis of cancer. In both of the former and latter cases, since the endscope CCD camera performs photographing while moving in the advancing direction (i.e., the axial direction) of the tubular organ, an obtained image becomes a doughnut-like image just as one obtained by photographing a tunnel. In order to photograph the state of the inner wall in detail, the CCD-camera needs to be rotated in the circumferential direction of the tube, followed by photographing. However, such operation is not actually achieved in a human body in consideration of a pain of a patient.

In such a case, although it is very convenient to display or print the photographed video image (i.e., the doughnut-like image) of the inner wall of the tubular organ as a developed continuous still image, for now, there exists no such system for automatically converting the video image of the inner wall of the tubular organ into the continuous developed still image.

SUMMARY OF THE INVENTION

In view of the above-described problems observed in the prior art, an object of the present invention is to provide a system for automatically generating a seamless and continuous developed still image with less-distortion by generating a developed diagram in the circumferential direction of a tube based on one frame of a video image of the inner wall of a tubular object photographed while moving in the axial direction of the tubular object, and then, stitching the developed diagrams in the longitudinal direction (i.e., on a central axis) of the tube by mosaic processing.

The present invention is directed to solve the above-described problems, and further, the above-described object can be attained by a system for automatically generating a continuous developed still image from a video-image of an inner wall of a tubular object photographed while moving in the axial direction of the tubular object, comprising: digital image data capturing means for capturing video image data as digital image data from a recording medium having recorded thereon the video image data of an inner wall of a tubular object; pipe projection converting means for creating a developed diagram in the circumferential direction of the inner wall of the tubular object with respect to each of frames of the captured digital image data; mosaic processing means for subjecting the developed diagram of each of the frames created by the pipe projection converting means to mosaic processing, to convert it into continuous and seamless developed still image data; image data compressing means for compressing the developed still image data; and compressed image data storing means for storing the compressed image data obtained by compressing the developed still image data; wherein the mosaic processing means is of a type for cutting out and stitching strips of the developed diagram of each of the frames.

Furthermore, the above-described object of the present invention can be more effectively attained by a system for automatically generating a continuous developed still image from a video image of an inner wall of a tubular object photographed while moving in the axial direction of the tubular object, comprising: digital image data capturing means for capturing video image data as digital image data from a recording medium having recorded thereon the video image data of an inner wall of a tubular object; pipe projection converting means for creating a developed diagram in the circumferential direction of the inner wall of the tubular object with respect to each of frames of the captured digital image data; mosaic processing means for subjecting the developed diagram of each of the frames created by the pipe projection converting means to mosaic processing, to convert it into continuous and seamless developed still image data; image data compressing means for compressing the developed still image data; compressed image data storing means for storing the compressed image data obtained by compressing the developed still image data; and data registering means for storing the compressed image data in the compressed image data storing means, to generate a database; wherein the mosaic processing means is of a type for cutting out and stitching strips of the developed diagram of each of the frames.

As described above, with the system for automatically generating the continuous developed still image from the video image of the inner wall of the tubular object according to the present invention, since the movement quantity or direction of the image can be obtained by calculation based on the image data, thereby making it unnecessary to acquire the attitude information of the camera, so as to dispense with a special camera, unlike in the prior art. Furthermore, since the width of the strip to be cut is adjusted according to the movement quantity, it becomes unnecessary to move the camera at a constant speed at the time of photographing, thereby making it unnecessary to use a special photographing technique or provide a special photographing apparatus, so as to produce the effect of shortening of a photographing time.

Moreover, since the developed still image is automatically generated in accordance with a program while all of the frames are subjected to the mosaic processing, it becomes unnecessary to classify the frames to be subjected to the mosaic processing, so as to produce the effect of shortening of a mosaic processing time.

Additionally, since the mosaic processing for stitching only the strips of the least distorted portion of the frame image is adopted, it is possible to generate the continuous developed still image with less-distortion, so as to produce the effect of accurate examination of the state of the inner wall of the tubular object.

As a broad summary, this writing discloses the following.

An image processing system automatically generates a seamless and continuous developed still image with little distortion by creating a developed diagram in the circumferential direction of a tube from one frame of a video image of an inner wall of a tubular object photographed by a video camera while moving in the axial direction of the tubular object and stitching the developed diagrams with each other in the longitudinal direction (i.e., on a central axis) of the tube by mosaic processing. The system is provided with: a digital image data capturer for capturing video image data as digital image data from a recording medium having recorded thereon the video image data; a pipe projection converter for creating a developed diagram in the circumferential direction of the inner wall of the tubular object with respect to each of frames of the captured digital image data; a mosaic processor for subjecting the developed diagram of each of the frames created by the pipe projection converter to the mosaic processing, to convert it into continuous and seamless developed still image data; an image data compressor for compressing the developed still image data; and a compressed image data storage for storing the compressed image data obtained by compressing the developed still image data; wherein the mosaic processor is of a type for cutting out and stitching strips of the developed diagram of each of the frames.

DETAILED DESCRIPTION OF THE PREFERRED EMBODIMENT

A preferred embodiment according to the present invention will be described below with reference to the accompanying drawings.

Figure 1:
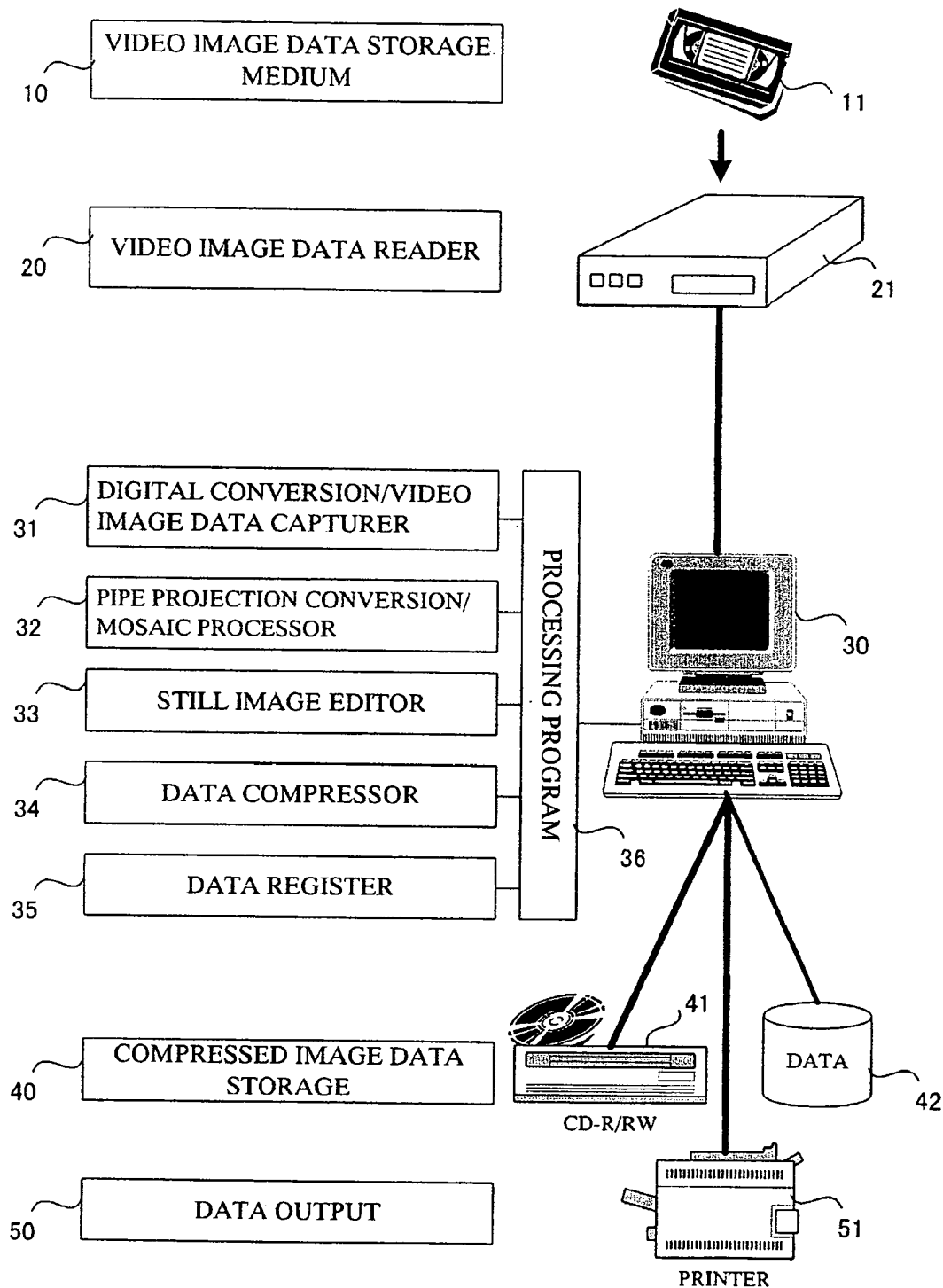
FIG. 1 is a diagram illustrating one example of the configuration of a system for automatically generating a continuous developed still image from a video image of an inner wall of a tubular object according to the present invention.

FIG. 1 is a diagram illustrating one example of the configuration of a system according to the present invention. A personal computer 30 is an essential component of the system, and includes a digital conversion/video image data capturer 31, a pipe projection conversion/mosaic processor 32, a still image editor 33, a data compressor 34, a data register 35 and a processing program 36.

A videocassette recorder 21 connected to the personal computer 30 is one example of a video image data reader 20, which reads video image data on an inner wall of a tubular object photographed by a video camera, not shown, and recorded in a video tape 11 exemplifying a video image data storage medium 10, and then, transmits it as a data signal to the personal computer 30.

A CD-R/RW drive 41 and a hard disk 42, both of which are connected to the personal computer 30, exemplify a compressed image data storage 40. Furthermore, a printer 51 is one example of a data output 50 for printing and outputting a developed still image which is formed.

Here, in the case where the videocassette recorder 21 is of a digital type, video image data is captured into the personal computer 30 as it remains a digital signal by the use of an interface such as IEEE1394. If the personal computer 30 is a Microsoft's Windows-compatible computer, data is temporarily stored in an inside memory in an AVI (Audio Video Interleave) format. In contrast, in the case where the videocassette recorder 21 is of an analog type (for example, of an S-VHS type), a video capture board is used in the digital conversion/video image data capturer 31, so that analog image data can be converted into a digital image data, to be thus captured into the personal computer 30.

The pipe projection conversion/mosaic processor 32 is adapted to form the developed still image based on the captured video image data in accordance with special software. This mosaic processing can be performed by a mosaicing method disclosed in International Application Laid-open No. WO 98/34195 internationally laid open to the public under the provision of Section 21 of Patent Cooperation Treaty (hereinafter abbreviated as "PCT").

The still image editor 33 is adapted to adjust the coloration, contrast, brightness and the like of a panoramic image obtained by the mosaic processing. Commercially available image editing softwares can be used as the still image editor 33. For example, "Adobe Photoshop" (registered trademark) available from Adobe Systems Incorporated can be used.

The data compressor 34 is adapted to compress the data, so as to reduce the size of the image for the purpose of the formation of a database of the image. In the present preferred embodiment, the compression is performed in accordance with software. Typical compression image file formats include JPEG, GIF, TIFF and the like.

The data register 35 is adapted to add the name of an object to be photographed, a photographing place, a photographing time, a registered date and the like as attached data in order to facilitate the retrieval of the still image when the database is formed. Commercially available database softwares can be used as the data register 35. For example, "Microsoft Access" (registered trademark) available from Microsoft Corporation can be used.

The processing program 36 is responsible for allowing the personal computer 30 to exhibit the functions possessed by the above-described components.

Figure 2:
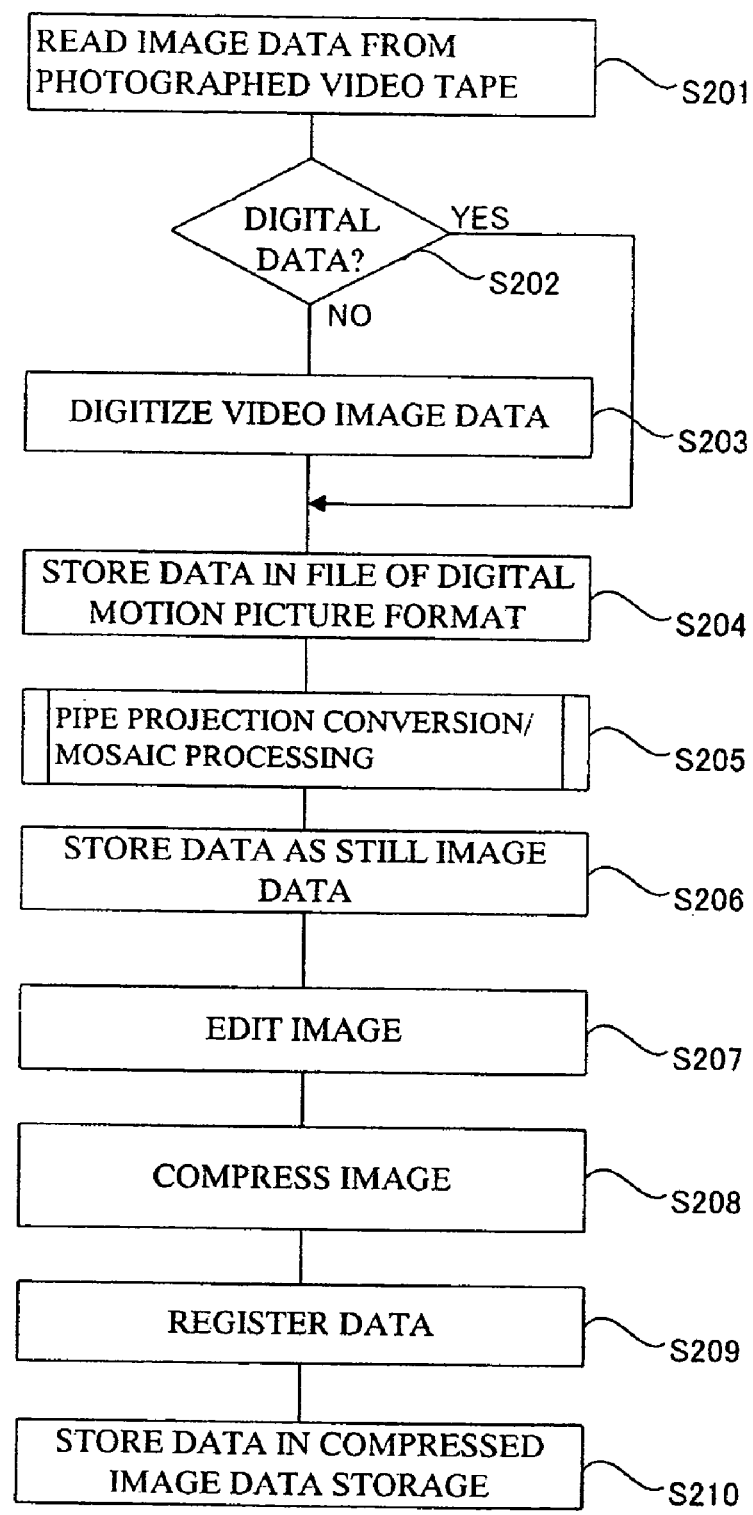
FIG. 2 is a flowchart illustrating one example of the system for automatically generating the continuous developed still image from the video image of the inner wall of the tubular object according to the present invention.

FIG. 2 is a flowchart illustrating operation performed by the personal computer 30 in accordance with the processing program 36. Explanation will be made below in reference to FIG. 2.

First, in step S201, the image data is read from the photographed videotape by the videocassette recorder. In the case where the image data is analog data, it is converted into digital data in step S203. In step S202, in the case where it is determined that the image data is digital data, the digital data is captured into the personal computer as it is, and then, it is stored in a hard disk in a digital motion picture file format (for example, the AVI format) (step S204).

Figure 3:
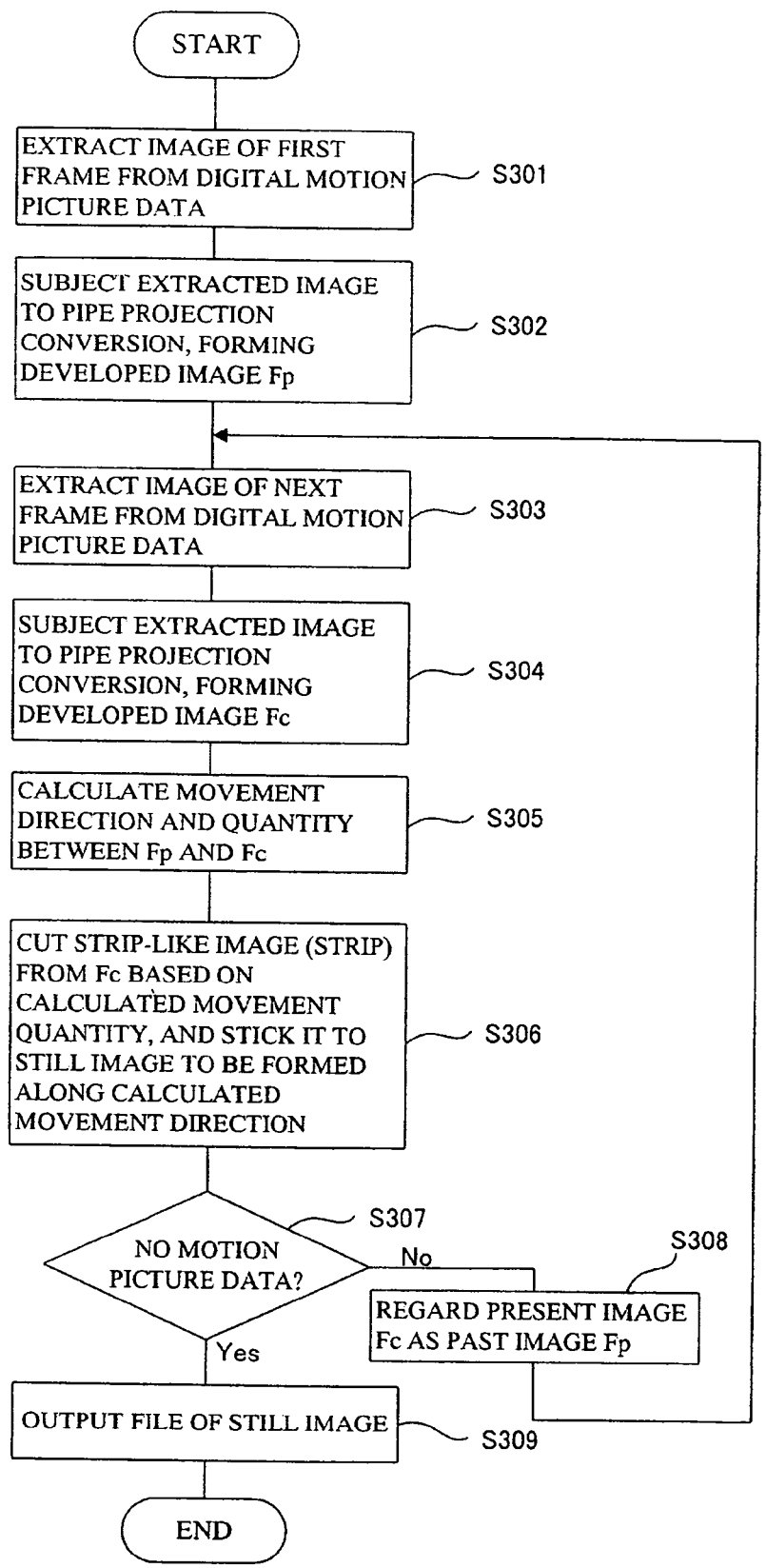
FIG. 3 is a flowchart illustrating one example of pipe projection conversion/mosaic processing.
Figure 4:
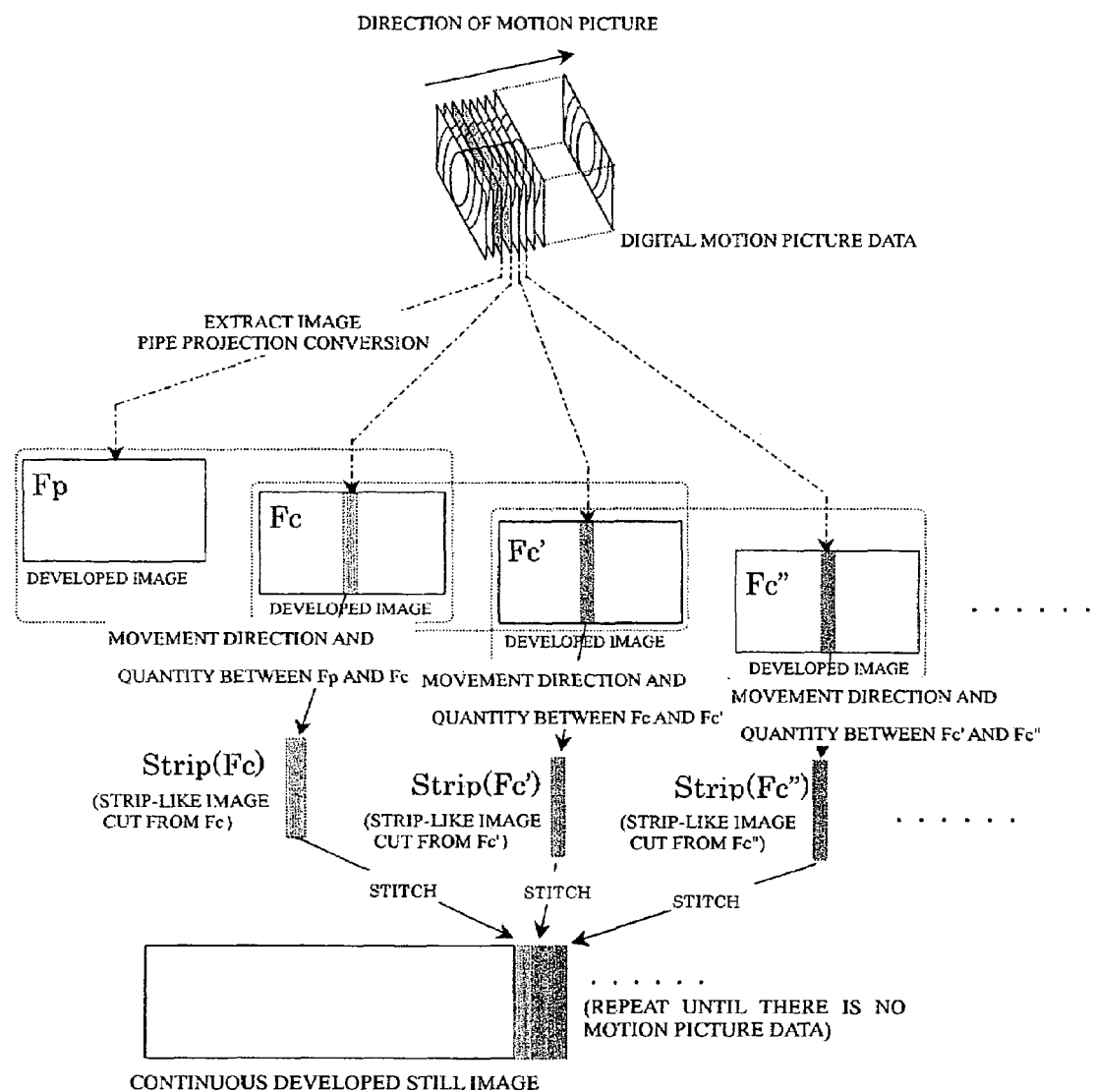
FIG. 4 is a diagram illustrating the concept of the mosaic processing in the system for automatically generating the continuous developed still image from the video image of the inner wall of the tubular object according to the present invention.

Next, in step S205, the pipe projection conversion is performed with respect to each of frames of the image data, so that a developed diagram is created, followed by the mosaic processing in which strips (strip-like images) are cut from the developed diagram and stitched with each other in accordance with the mosaic processing. FIG. 3 is a flowchart illustrating the processing in step S205; and FIG. 4 is a diagram illustrating the concept.

In step S206, the strips are stored in the hard disk as the still image data (for example, in a BMP file format). Thereafter, as required, the quality of the image is adjusted in accordance with image editing software in step S207. In contrast, as not required, the control routine proceeds to step S208, in which the image is compressed and stored as the compressed image data. The file formats include JPEG, GIF, TIFF and the like.

Subsequently, in step S209, data registration is performed for adding data such as the name of the object to be photographed, the photographing place, the photographing time, the registered date and the like to the compressed image data. In addition, in step S210, the data is stored in an inside hard disk or the compressed image data storage such as an outside CD or MO, thereby completing the formation of the database.

FIG. 3 is a flowchart illustrating the processing in the above-described step S205, which is the subject matter of the present invention. A description will be given below in detail.

First, in step S301, an image of a first frame is extracted from the digital motion picture data. In step S302, the extracted image is subjected to the pipe projection conversion, thereby forming a developed image. The developed image is designated by Fp.

Figure 5:
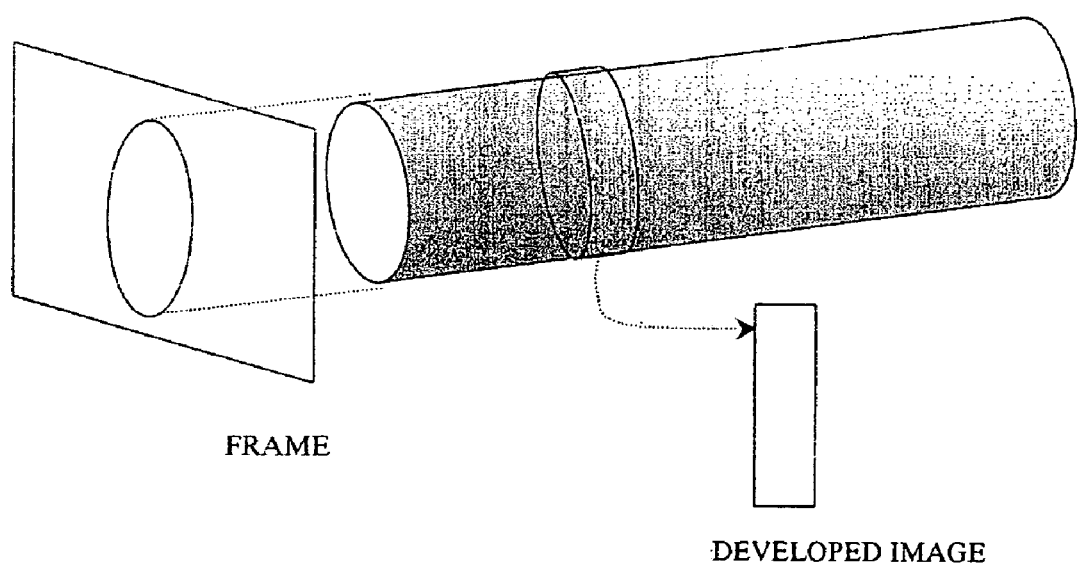
FIG. 5 is a diagram illustrating the concept of pipe projection.
Figure 6:
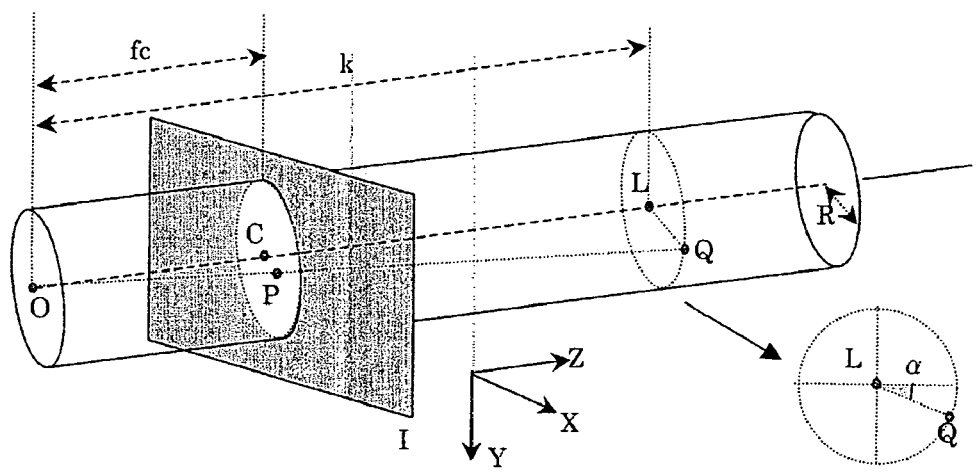
FIG. 6 is a diagram illustrating the principle of pipe projection conversion.

Here, the pipe projection refers to the projection of an image screen (in which an inner wall surface is reflected in a doughnut-like form) on a three-dimensional cylinder crossing the image screen, as illustrated in FIG. 5, and then, the development of a part of the projected cylinder to a rectangular image. The principle of the formation of the developed diagram is as follows:

First of all, the projection of the image to the three-dimensional cylinder (hereinafter referred to as a "pipe") is considered. The relationship between the image and the pipe is set as illustrated in FIG. 6. Reference character I designates the image obtained by photographing the pipe; and reference character R designates the radius of the pipe. The axis of the pipe is selected in such a manner as to pass through an optical center O and a focusing point C (cx, cy) of a camera (here, for the sake of simplification, it is construed that a Z axis in absolute coordinates is parallel to the axis of the pipe). Reference character fc designates a focal distance. Each image point P (x, y, fc) on the image I is projected on a corresponding point Q on the pipe. The point Q is aligned with the optical center O and the image point P. A point L is located as a projected point of the point Q on the axis of the pipe. Reference character k designates a distance between the point L and the optical center O. Moreover, a represents an angle formed between a line connecting the point L to the point Q and a line parallel to the X axis in the absolute coordinates and passing the point L. At this time, the point Q on the pipe can be expressed by the following equation (1):

$$Q(Qx, Qy, Qz) = (R \cos \alpha, R \sin \alpha, k) \quad (1)$$

Additionally, the point P on the image screen with respect to the point Q can be expressed by the equation (2) below by using the focal distance fc and the distance k:

$$P(x, y, fc) = (fc/k*Qx, fc/k*Qy, fc) \quad (2)$$

In unifying the above-described equations, the point P can be expressed by the equation (3) below with respect to fc, k, R and $\alpha$.

$$P(x, y, fc) = (fc/k*R \cos \alpha, fc/k*R \sin \alpha, fc) \quad (3)$$

Figure 7:
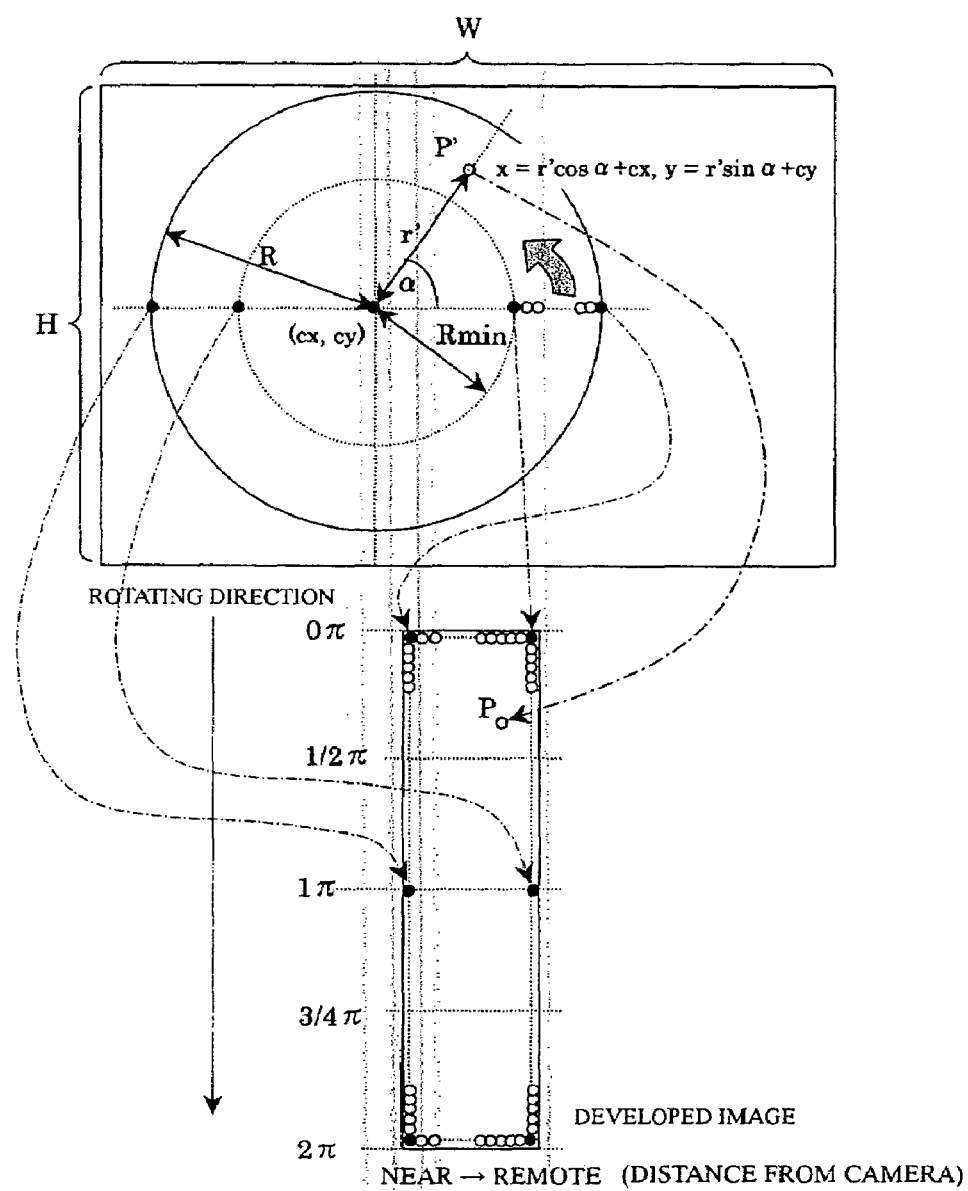
FIG. 7 is a diagram illustrating the creation of a developed diagram by the pipe projection conversion.

FIG. 7 illustrates an actually developed state. The width of the developed image is calculated in accordance with the following expression:

$$fc*(R-Rmin)/Rmin$$

by using the radius R and Rmin of the pipe reflected on the image I before the development and the focal distance fc (here, the radius Rmin refers to "the pipe minimum radius of an object to be developed". In performing the pipe projection, the actual photographing distance becomes remote as the object to be developed is located nearer the center of the pipe, thereby reducing resolution at the time of the development. Consequently, it is necessary to develop the image by setting the radius Rmin to an appropriate value.). In addition, the height of the developed image is equal to the length of a circumference having the radius R of the pipe (i.e., $2\pi R$). Here, if an arbitrary point on the developed image is represented by P(x, y), the pipe projection can be achieved by obtaining a point P' on the image I corresponding to each of the points P, and copying pixel data on the point P'. A pixel at a left end of the developed image corresponds to a pixel on the circumference having the radius R of the image I; in contrast, a pixel at a right end of the developed image corresponds to a pixel on the circumference of the radius Rmin of the image I.

Figure 8:
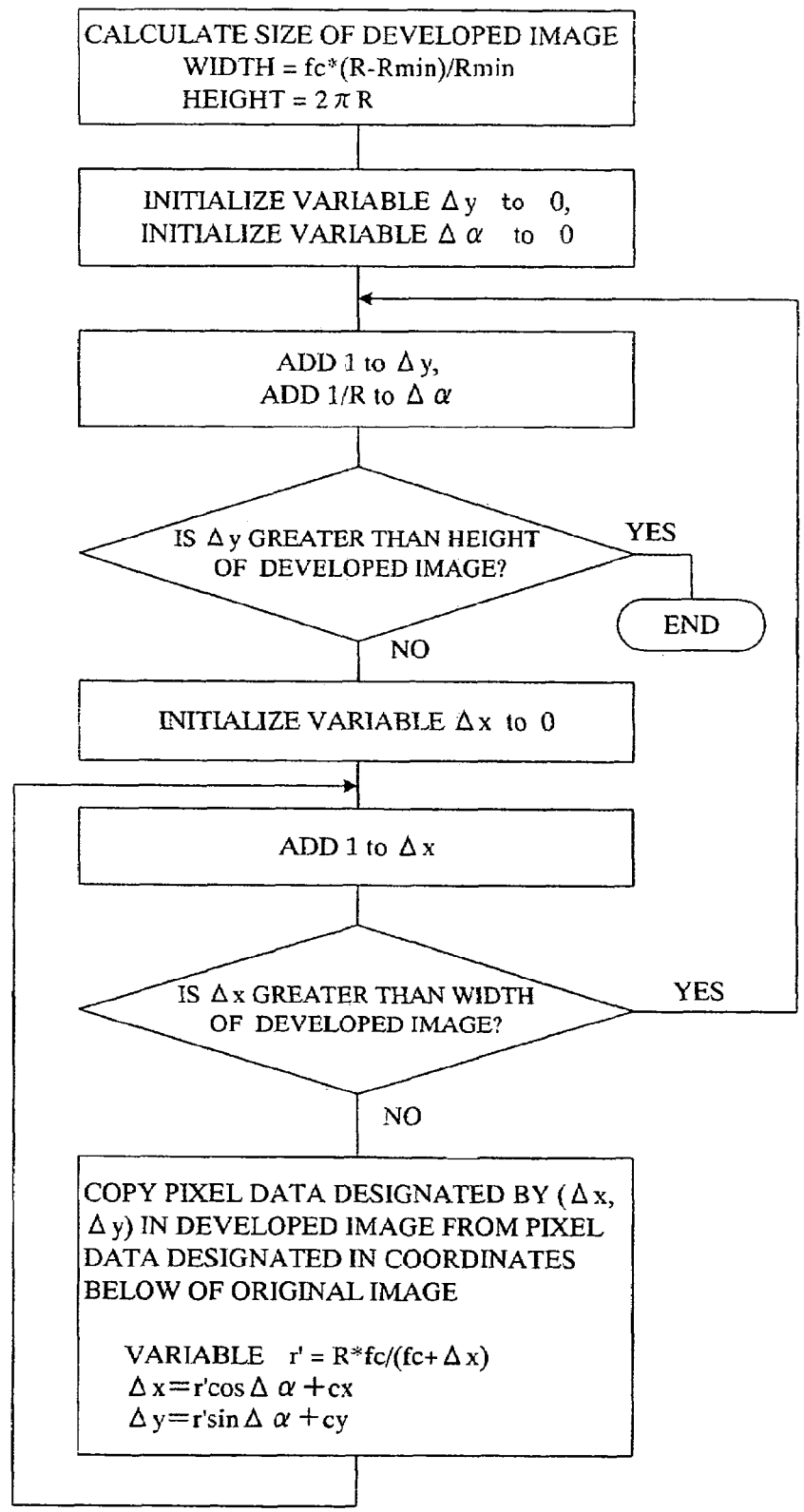
FIG. 8 is a flowchart illustrating one example of the creation of the developed diagram by the pipe projection conversion.

FIG. 8 is a flowchart illustrating one example of the pipe projection conversion processed by the use of the computer, although the explanation will be omitted below.

Subsequently, in step S303, an image of a second frame is extracted from the digital motion picture data. In step S304, the extracted image is subjected to the pipe projection conversion, thereby forming a developed image, which is designated by Fc.

Next, in step S305, the movement quantity and direction between the developed images Fp and Fc are calculated. Incidentally, although the movement quantity and direction between the developed images Fp and Fc are calculated by the use of algorithm in accordance with an "optical flow constraint equation" in the present preferred embodiment, the present invention is not restricted to such algorithm.

Subsequently, in step S306, a strip-like image (hereinafter referred to as a "strip". Since the strip is cut from a portion of the image with least distortion, it is normally the center of the image.) is cut from the developed image Fc based on the calculated movement quantity, and is stuck to a still image to be formed along the calculated movement direction. This is referred to as the mosaic processing. The width of the strip to be cut becomes greater as the movement quantity is larger; in contrast, it becomes smaller as the movement quantity is smaller. The data in the movement direction is used for positioning when the preceding and following images are stuck to each other.

In this manner, since the movement quantity and direction of the image can be obtained by the calculation based on the image data according to the present invention, it becomes unnecessary to acquire the attitude information of the camera, thereby dispensing with a special camera, unlike in the prior art. Furthermore, since the width of the strip to be cut is adjusted according to the movement quantity, it becomes unnecessary to move the camera at a constant speed in photographing, thereby obviating special photographing technique or device, so as to shorten a photographing time.

Next, the present developed image (i.e., the second image) Fc is referred to as the developed image Fp (step S308). The control routine returns to step S303, in which an image of a third frame is extracted. In step S304, the extracted image is subjected to the pipe projection conversion, thereby forming a developed image, which is designated by Fc.

Subsequently, in step S305, in the same manner, the movement quantity and direction between the developed images Fp and Fc are calculated.

Next, in step S306, a strip is cut from the developed image Fc based on the calculated movement quantity, and then, is stuck to the immediately preceding strip along the calculated movement direction.

Hereinafter, the control routine is repeated until there is no image data (FIG. 4).

When the pipe projection conversion/mosaic processing is completed with respect to all of the frames of the image data, the control routine proceeds to step S309, in which the formed developed still image file is temporarily stored in the hard disk in the computer 30 as the still image data (step S206 in FIG. 2).

What is claimed is:

1. A system for automatically generating a continuous developed still image from a video image of an inner wall of a tubular object photographed while moving in the axial direction of the tubular object, the system comprising:
    digital image data capturing means for capturing video image data as digital image data from a recording medium having recorded thereon the video image data;
    pipe projection converting means for creating a developed diagram in the circumferential direction of the inner wall of the tubular object with respect to each of frames of the captured digital image data;
    mosaic processing means for subjecting the developed diagram of each of the frames created by the pipe projection converting means to mosaic processing, to convert it into continuous and seamless developed still image data;
    image data compressing means for compressing the developed still image data; and
    compressed image data storing means for storing the compressed image data obtained by compressing the developed still image data;
    wherein the mosaic processing means is of a type for cutting out and stitching strips of the developed diagram of each of the frames.

2. A system for automatically generating a continuous developed still image from a video image of an inner wall of a tubular object photographed while moving in the axial direction of the tubular object, the system comprising:
    digital image data capturing means for capturing video image data as digital image data from a recording medium having recorded thereon the video image data;
    pipe projection converting means for creating a developed diagram in the circumferential direction of the inner wall of the tubular object with respect to each of frames of the captured digital image data;
    mosaic processing means for subjecting the developed diagram of each of the frames created by the pipe projection converting means to mosaic processing, to convert it into continuous and seamless developed still image data;
    image data compressing means for compressing the developed still image data;
    compressed image data storing means for storing the compressed image data obtained by compressing the developed still image data; and
    data registering means for storing the compressed image data in the compressed image data storing means, to generate a database;
    wherein the mosaic processing means is of a type for cutting out and stitching strips of the developed diagram of each of the frames.

3. A system for automatically generating a continuous developed still image from a video image of an inner wall of a tubular object according to claim 1, wherein the tubular object is a tunnel.

4. A system for automatically generating a continuous developed still image from a video image of an inner wall of a tubular object according to claim 2, wherein the tubular object is a tunnel.

5. A system for automatically generating a continuous developed still image from a video image of an inner wall of a tubular object according to claim 1, wherein the tubular object is a pipe.

6. A system for automatically generating a continuous developed still image from a video image of an inner wall of a tubular object according to claim 2, wherein the tubular object is a pipe.

7. A system for automatically generating a continuous developed still image from a video image of an inner wall of a tubular object according to claim 1, wherein the tubular object is a tubular organ of a human being or an animal.

8. A system for automatically generating a continuous developed still image from a video image of an inner wall of a tubular object according to claim 2, wherein the tubular object is a tubular organ of a human being or an animal.

* * * * *